United States Patent [19]

Zinger

[11] Patent Number: 5,578,016
[45] Date of Patent: Nov. 26, 1996

[54] STOPCOCK

[75] Inventor: Freddi Zinger, Raanana, Israel

[73] Assignee: Elcam Plastic Kibbutz Bar-Am, Hagalil, Israel

[21] Appl. No.: 507,043

[22] Filed: Jul. 25, 1995

[30] Foreign Application Priority Data

Jul. 29, 1994 [IL] Israel ........................... 110508

[51] Int. Cl.$^6$ ........................................... A61B 5/00
[52] U.S. Cl. ................ 604/248; 604/236; 137/625.12
[58] Field of Search ............................ 604/118, 167, 604/236, 246, 247, 248; 137/625.12, 625.13, 625.17, 625.18

[56] References Cited

U.S. PATENT DOCUMENTS

| | | | |
|---|---|---|---|
| 2,261,213 | 11/1941 | Bierman | 604/236 X |
| 2,646,042 | 7/1953 | Hu | 604/118 X |
| 2,854,027 | 9/1958 | Kaiser et al. | 604/248 X |
| 3,185,179 | 5/1965 | Harautuneian | 604/248 X |
| 3,344,785 | 10/1967 | Hamilton . | |
| 3,834,372 | 9/1974 | Turney | 604/248 X |
| 3,952,729 | 4/1976 | Libman et al. | 604/236 X |
| 4,967,797 | 11/1990 | Manska | 604/248 X |
| 5,334,163 | 8/1994 | Sinnett | 604/236 |
| 5,376,071 | 12/1994 | Henderson | 604/246 X |
| 5,439,452 | 8/1995 | McCarty | 604/248 |

FOREIGN PATENT DOCUMENTS 2005807 4/1979 United Kingdom .

*Primary Examiner*—Sam Rimell
*Attorney, Agent, or Firm*—Brumbaugh, Graves, Donohue & Raymond

[57] ABSTRACT

A stopcock comprises a tubular outer body having at least two radial openings being on the same transverse cross-sectional plane of said body; and a hollow core member snugly fitting into said outer body and having a first open end and a second, closed end, said member being connected to or integral with a handle at said second end; said member having at least one radial bore; and being rotatable within said body between a first state in which said bore is in register with a first of said at least two openings and a second state in which said bore is in register with a second of said at least two openings.

4 Claims, 4 Drawing Sheets

STOPCOCK

FIELD OF THE INVENTION

The present invention concerns a device which may serve as a component of fluids' infusion systems. More specifically, the present invention provides a stopcock for regulating flow of fluids, both gas and liquid, in a medical infusion system, particularly such intended for use in a laparoscopic surgery system.

BACKGROUND OF THE INVENTION

Stopcocks are a common and essential component of medical infusion equipment as they allow the linking of tubes of an infusion system to different inlet or outlet tubes. Such stopcocks, which may be made of plastic, glass or metal, typically comprise an outer tubular body provided with two or more luer type connectors and, rotatable therein, a solid core member provided with bores adapted to come into register with the lumen of the luer connectors and allow transfer of fluid from one connector to another. The core member is connected or integral with a handle which allows the user to select between different states.

Luer connectors in medical devices must conform with international standards as regards their inner and outer dimensions. This limits their lumen diameter to a maximum of about 3.0 mm, which in turn limits the maximum flow rate. In various medical procedures in which a slow fluid flow rate is required, this is not a serious handicap, whereas in others this fact is disadvantageous necessitating use of various other accessories. In laparoscopic surgery, for example, a body cavity, e.g. the peritoneum, is first inflated with a gas such as $CO_2$ which process is termed "insufflation". Insufflation is a rather slow process, in contrast the release of the gas from the body cavity, which process is termed "disufflation", which is usually a very fast process, lasting a few seconds. In principle, conventional stopcocks could be used for such a procedure, i.e. the connector connected to the duct leading to the body cavity (the "body duct"), being linked to a connector connected to the duct leading to the gas source (the "gas duct") during insufflation, and switched so as to be linked to an opening from which the gas is discharged (the "gas discharge opening"), during disufflation; however, the diameter of the lumen of the luer connector of conventional stopcocks as well as the diameter inside the core member of conventional stopcocks, is unduly limiting the rate flow of the same during the disufflation step, and therefore, conventional stopcocks are not used or used only to a limited extent in such a procedure.

GENERAL DESCRIPTION OF THE INVENTION

The present invention provides a stopcock of a novel design. In accordance with a preferred embodiment of the invention, the stopcock is adapted for use in laparoscopic surgery system. In accordance with this preferred embodiment, the stopcock has at least two states selectable by the user: an insufflation state in which a connector connected to the body duct is linked to the connector connected to the gas duct; and a disufflation state in which the body duct connector is linked to a discharge opening, having a substantially larger diameter than the gas duct connector.

The present invention provides a stopcock comprising:

a tubular outer body having at least two radial openings (preferably of circular cross-sectional shape) being on the same transverse cross-sectional plane of said body; and a hollow core member snugly fitting into said outer body and having a first open end and a second, closed end, said member being connected to or integral with a handle at said second end; said member having at least one radial bore; and being rotatable within said body between a first state in which said bore is in register with a first of said at least two openings and a second state in which said bore is in register with a second of said at least two openings.

The diameter of the lumen of the hollow core member can be any chosen diameter and is not limited to the diameter of the luer connector as in conventional stopcocks. This may be used to advantage in allowing a differential flow rate at different operational states of the stopcock. For example, the first opening may be fitted with a luer connector of a conventional type, permitting flow of fluids in or from the lumen of the core member which connect to a duct at its open end at a rate limited by the diameter of the luer connector, and the second opening may be of a substantially larger diameter. In order to achieve this feat, the bore in said core member will have a diameter at least that of said second opening. The maximal flow rate is obviously limited by the diameter of the lumen of the hollow core which should thus also be the same or larger than that of the second opening.

A preferred embodiment of the invention, as pointed out above, is a stopcock adapted for use in a laparoscopic surgery system. The invention will at times be described with specific reference to this preferred embodiment it being understood that the invention is not limited thereto.

In accordance with this preferred embodiment, a first of said openings in the tubular outer body is fitted with a radially extending luer connector having typically an inner diameter of about 2–3 mm, and a second of said openings is a discharge opening, of a larger diameter than the inner diameter of the luer connector. In this preferred embodiment, the duct to the opening at said one end of the hollow core member is connected to the body duct, and the luer connector is connected to the gas duct.

In the insufflation state of the device according to the preferred embodiment, said bore is in register with the luer connector whereupon gas flows into the hollow lumen of the core member and from there into the body duct, i.e. leading gas to a body cavity such as the peritoneum, whereupon the body cavity is inflated. In the disufflation state, the bore is brought to be in register with the discharge opening (which, as pointed out above has a larger diameter than the luer connector) and thus gas expressing from the body cavity through the body duct enters the lumen of the hollow core member, and then escapes out of this gas discharge opening.

In the following, the invention will be illustrated by a description of some non-limiting specific embodiments, with reference to the annexed drawings.

3

Figure 5:
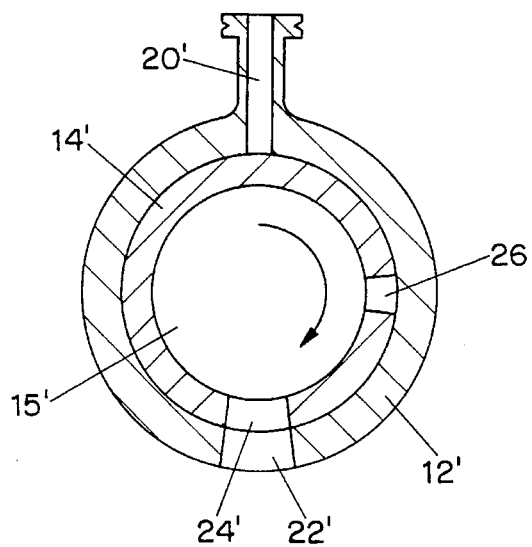
FIG. 5 is a cross-sectional view along line III—III in FIG. 4 showing the stopcock in a first position.
Figure 6:
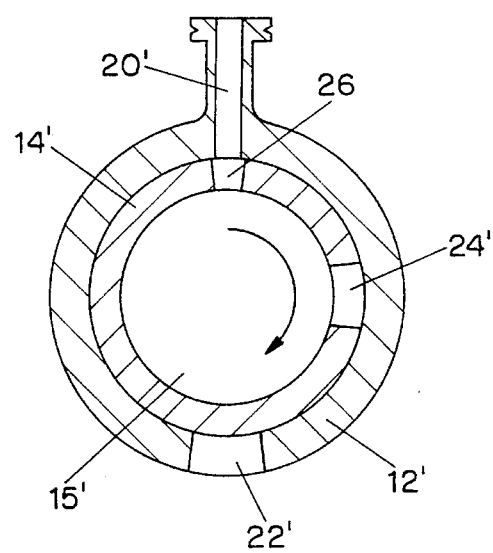
Figure 7:
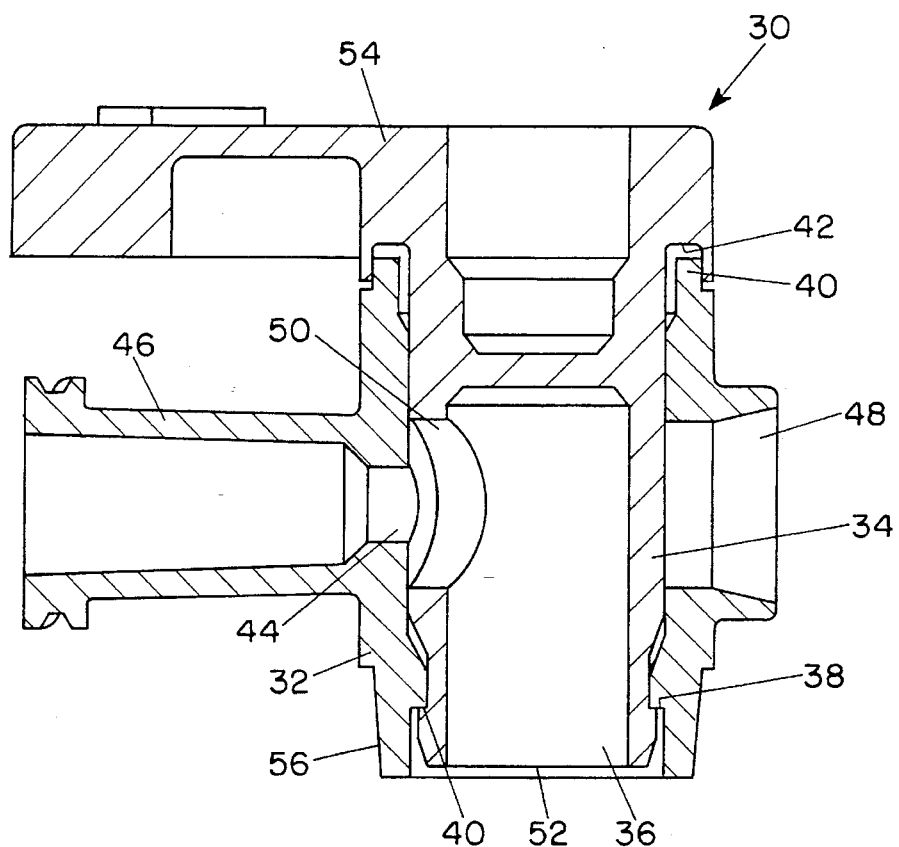
Figure 8A:
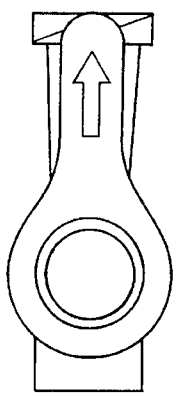
Figure 8B:
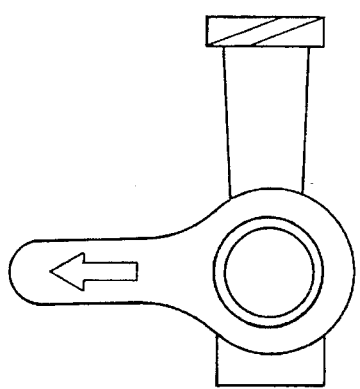
Figure 8C:
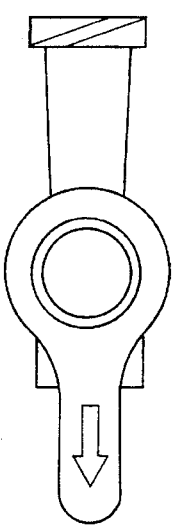
Figure 9:
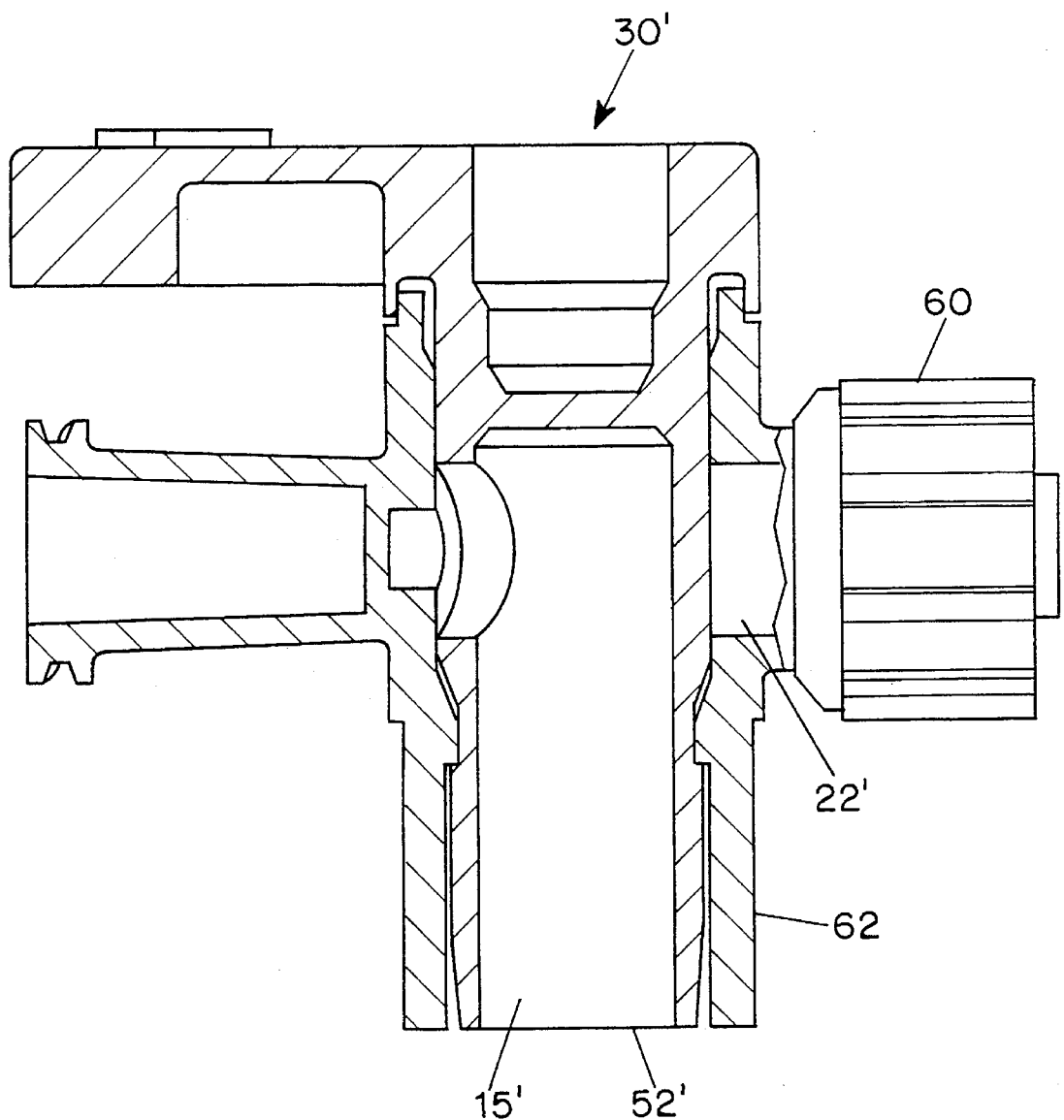

FIG. 6 is a cross-section similar to that of FIG. 5 showing the stopcock in a second position;

FIG. 7 shows a longitudinal cross-section through a specific embodiment of a stopcock of the invention;

FIG. 8 is a view from the direction of arrow VIII in FIG. 7 showing the stopcock in three operational states: insufflation state (FIG. 8a), an intermediate, "OFF" state (FIG. 8b), and a disufflation state (FIG. 8c) and FIG. 9 is a partial cross-section of a stopcock according to another embodiment of the present invention.

DETAILED DESCRIPTION OF SPECIFIC EMBODIMENTS

Figure 1:
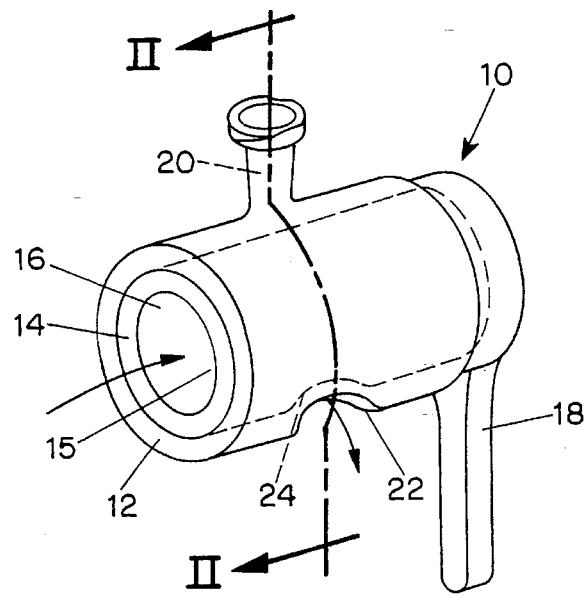
FIG. 1 is a perspective view of a stopcock according to one embodiment of the invention.
Figure 2:
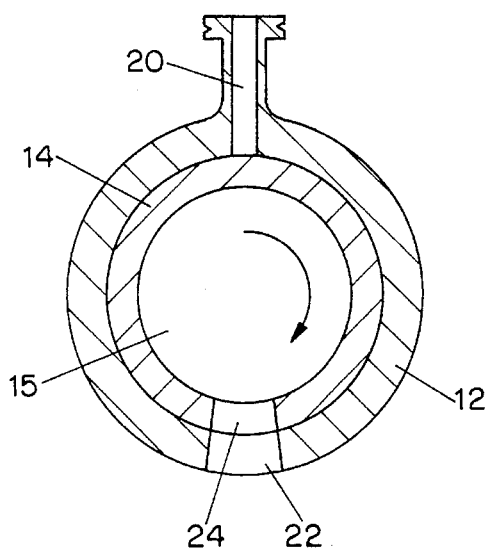
FIG. 2 is a cross-sectional view along line II—II in FIG. 1, showing the stopcock in a first position.
Figure 3:
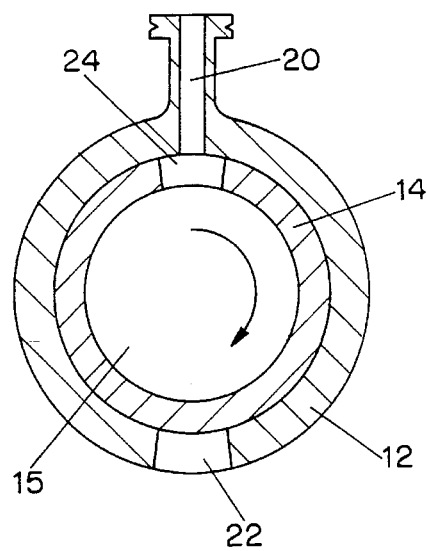
FIG. 3 is a cross-section similar to that of FIG. 2 showing the stopcock in a second position.

Stopcock 10 shown in FIGS. 1–3 comprises a tubular outer body 12 and a core member 14 having a lumen 15, snugly fitting into said outer body. Lumen 15 is open at end 16 and closed at the other end which is fitted with an integral handle 18. Core member 14 is rotatable within tubular body 12 by means of handle 18.

Tubular body 12 has two radial openings opposite one another, one being a female luer type connector 20 and a discharge opening 22 having a substantially larger diameter than the inner diameter of the luer connector. Connector 20 and opening 22 are on the same transverse cross-sectional plane. Typically, the lumen of the luer connector has a diameter of about 2–3 mm whereas the diameter of the discharge opening is about 5 mm. Core member 14 has a radial bore 24 extending out from lumen 15 and having a diameter essentially the same as that of the discharge opening 22.

In accordance with a preferred embodiment of the invention, the stopcock is used in a laparoscopic surgery system. In this kind of application, lumen 15 is connected to a body duct whereas luer connector 20 is connected to a gas duct. By rotation of core member 14, the lumen may be connected either to the luer connector 20 or to the discharge opening 22 for insufflation or disufflation, respectively. In the disufflation state, shown in FIG. 2, bore 24 is in register with opening 22 whereupon gas can flow through lumen 15 out of opening 22, as represented by the arrows in FIG. 1. For insufflation, the handle is rotated by 180° whereupon bore 24 comes to be in register with luer connector 20 and gas can flow into lumen 15 from the gas duct (not shown), thus inflating the body cavity.

Figure 4:
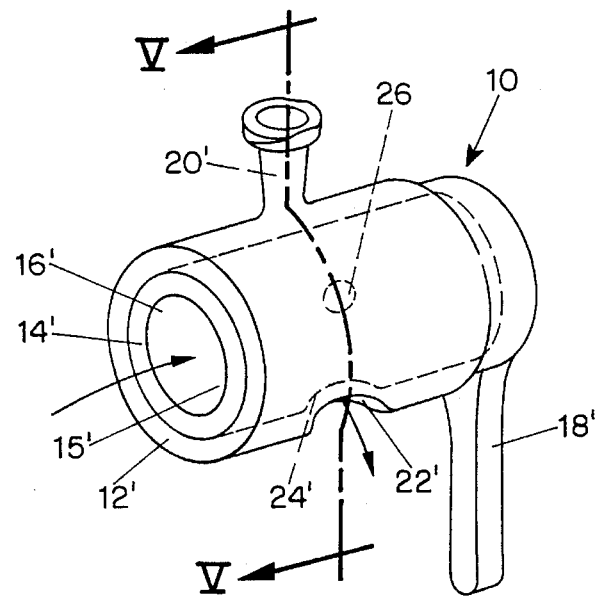
FIG. 4 is a perspective view of a stopcock according to another embodiment of the invention.

Reference is now being made to FIGS. 4 and 5 showing another embodiment of a stopcock of the invention. This stopcock is very similar to that shown in the embodiment of FIGS. 1–3 and the same reference numerals were used with a prime indicator for like elements; the reader is thus referred to the description of the embodiment of FIGS. 1–3 for their explanation. The difference between the stopcock of the embodiment shown in FIGS. 4–6 versus that of FIGS. 1–3 in that rather than a single bore 24 in the core member the core member 14' in the embodiment of FIGS. 4–6 has two bores, one 24' of a diameter essentially the same as discharge opening 22' and another, 26 of a diameter essentially the same as that of the inner diameter of luer connector 20'. Bores 26 and 24 are angularly disposed from one another on the same transverse cross-sectional plane, e.g. by about 90°. Thus, the switching between the disufflation state, shown in FIG. 5, to the insufflation state shown in FIG. 6, and vice versa, requires turning of handle 18' by less than 180°, e.g. by about 90°. As can be seen in FIG. 5, in the disufflation state, bore 24' is in register with opening 22', whereby gas coming from gas duct and entering lumen 15'

4 can egress through discharge opening 22'. In the insufflation state, shown in FIG. 6, radial bore 26 is in register with the lumen of connector 20' whereupon gas can flow from the gas duct (not shown) through lumen 15' and into the body cavity.

Reference is now being made to FIG. 7 showing a longitudinal cross-sectional view through a stopcock according to a specific embodiment of the invention. Stopcock 30 shown in FIG. 7 comprises a tubular outer body 32 and a core member 34 having a lumen 36. Tubular body 32 has shoulder means 38 and core member 34 has corresponding shoulder means 40 whereby body 32 and member 34 snap into engagement with one another. The longitudinal displacement of body 32 and member 34 versus one another is limited at the other end by means of matching ridge 40 and groove 42 in body 32 and member 34, respectively. Member 34 snugly fits into the lumen of body 32 and is rotatable about the longitudinal axis with respect thereto.

Tubular body 32 has two openings, one 44 fitted with a luer type connector 46 and another 48 which has a much wider diameter than opening 44.

Core member 34 has a radial opening 50. The lumen 36 of core member 34 is open at its one end 52 and closed at its other end where core member 34 is fitted with an integral handle 54. The entire stopcock 30 is suitably made of a plastic material such as polyethylene or polypropylene.

In use, end 52 is connected to a body duct (not shown) which has an adapter which fits around shoulders 56. A luer connector 46 is in turn connected to a gas duct.

In the position as shown in FIG. 7, opening 44 is in register with bore 50 whereupon gas can flow from the gas duct into lumen 36 and from there through the body duct into the body cavity. This state of the device, the insufflation state, is also shown in FIG. 8a. Following insufflation, the handle is rotated by 90° to the "OFF" position shown in FIG. 8b, in which it is retained during the performance of the laparoscopic surgery. Following the performance of the surgery, the handle may be rotated by another 90° to the position shown in FIG. 8c, whereupon bore 50 comes to be in register with opening 48 whereupon gas egressing from the body cavity can then be discharged through this opening.

FIG. 9 illustrates another embodiment of a stopcock 30' according to the present invention, differing from the embodiment of FIG. 7 only in that it comprises a luer "locknut" type connect 60 for connecting a suitable line (not shown) to a discharge opening 22' and a luer "slip" connector 62 for connecting a line (not shown) to the opening 52' of lumen 15' of the stopcock.

Fitting the stopcock with connectors at all its inlet and outlet openings permits its use in a plurality of applications as known per se.

It should be obvious to a person skilled in the art that connections other than those shown in the drawings and specifically described herein may be used for various applications.

I claim:

1. A stopcock comprising
   a tubular body having a first radial opening and a second radial opening, the radial openings being spaced apart circumferentially and being located in a common plane orthogonal to an axis of the tubular body, and the second radial opening having a diameter larger than the first radial opening;
   a hollow core member snugly received within the tubular body for rotation about the axis of the tubular body, the core member defining a lumen having an open end and a closed end, the core member having at least one radial bore located in the common plane of the radial openings in the tubular body and in communication with the lumen, and the lumen and a first bore of the at least one radial bore of the core member having diameters not less than the diameter of the second radial opening of the body; and handle means affixed to the core member adjacent the closed end of the lumen for rotating the core member between a first position in which a radial bore is in register with the first radial opening and a second position in which said first bore of the at least one radial bore is in register with the second radial opening.

2. A stopcock according to claim 1 wherein the first bore is the sole radial bore and is in register with the first radial opening when the core member is the first position.

3. A stopcock according to claim 1 wherein the first radial opening is associated with a luer connector affixed to the body and is adapted for introduction of a fluid into the lumen for delivery through the open end of the lumen when the core member is in the first position, and wherein the second radial opening is a discharge opening and is adapted for discharge of a fluid received through the open end of the lumen when the core member is in the second position.

4. A stopcock according to claim 1 wherein the at least one radial bore in the core member includes a second bore having a diameter that is not less than the diameter of the first radial opening in the body.

* * * * *